United States Patent [19]

Maurer et al.

[11] Patent Number: 5,873,900

[45] Date of Patent: *Feb. 23, 1999

[54] ELECTRONIC PAIN FEEDBACK SYSTEM AND METHOD

[75] Inventors: Donald D. Maurer, Marine on St. Croix; Michael L. Kalm, St. Louis Park; Alexander Kipnis, New Hope; Poonam Agarwala, New Brighton, all of Minn.

[73] Assignee: Empi, Inc., St. Paul, Minn.

[*] Notice: The term of this patent shall not extend beyond the expiration date of Pat. No. 5,653,739.

[21] Appl. No.: 877,970

[22] Filed: Jun. 18, 1997

Related U.S. Application Data

[62] Division of Ser. No. 527,811, Sep. 13, 1995, Pat. No. 5,653,739.

[51] Int. Cl.[6] ............................................. A61N 1/00
[52] U.S. Cl. ................................. 607/46; 128/898
[58] Field of Search ..................... 607/46, 50–52, 607/58, 63, 64; 600/554–557; 128/908, 898; 604/890.1, 891.1, 892.1, 31, 36, 65; 221/3

[56] References Cited

U.S. PATENT DOCUMENTS

| | | |
|---|---|---|
| 4,148,306 | 4/1979 | Mandl . |
| 4,166,452 | 9/1979 | Generales, Jr. ........................ 128/741 |
| 4,589,417 | 5/1986 | Eseifan et al. . |
| 4,711,248 | 12/1987 | Steuer et al. ............................ 128/748 |
| 4,763,666 | 8/1988 | Strain et al. ............................ 128/742 |
| 4,777,960 | 10/1988 | Berger et al. ........................... 128/706 |
| 4,857,716 | 8/1989 | Gombrich et al. .................. 129/695 X |
| 4,975,842 | 12/1990 | Darrow et al. .......................... 128/630 |
| 5,067,495 | 11/1991 | Brehm ...................................... 607/46 |
| 5,088,981 | 2/1992 | Howson et al. .......................... 604/31 |
| 5,104,374 | 4/1992 | Bishko et al. ........................... 604/31 |
| 5,314,423 | 5/1994 | Seney ....................................... 606/20 |
| 5,333,618 | 8/1994 | Lekhtman et al. ..................... 128/734 |
| 5,533,514 | 7/1996 | Lavigne et al. ........................ 128/744 |
| 5,653,739 | 8/1997 | Maurer et al. ........................... 607/46 |

OTHER PUBLICATIONS

*Assessment of Chronic Pain I. Aspects of the Reliability and Validity of the Visual Analogue Scale,* Anna Maria Carlsson, Elsevier Biomedical Press, 1983, pp. 87–101.

*Assessing Self–Report of Pain: A Comparison of Two Recording Procedures,* Frank L. Collins, Jr. and John E. Martin, Journal of Behavioral Assessment, 1980, pp. 55–63.

*Chronic Pain: Electromechanical Recording Device for Measuring Patients'Activity Patters,*Michael J. Follick, Ph.D. et al., Arch. Phys. Med. Rehabil. 1984, pp. 75–79.

*The Visual Analogue Scale: Its Use in Pain Measurement,* G.B. Langley and H. Sheppeard, Rheumatol International, 1984, pp. 145–147.

*The Measurement of Clinical Pain Intensity: A Comparison of Six Methods,* Deborah B. McGuire, Pain 27, 1986, pp. 117–125.

*Computerized Voiding Diary,*Jill M. Rabin, et al., Neurourology and Urodynamics, 1993, pp. 541–554.

*The Validation of Visual Analogue Scales as Ratio Scale Measures for Chronic and Experimental Pain,* Donald D. Price, et al., Pain 17, 1983, pp. 45–55.

*The Measurement of Clinical Pain,* Deborah B. McGuire, Nursing Research, 1983, pp. 152–156.

Primary Examiner—Jeffrey R. Jastrzab
Attorney, Agent, or Firm—Kinney & Lange, P.A.

[57] ABSTRACT

An electronic pain feedback system for use by a patient in determining the effectiveness of a pain treatment. The system includes an input device connected to a memory device. The input device includes a scale on which the patient enters perceived pain level data to initiate the pain treatment. The input device signals this data to the memory device where it is recorded. The electronic pain feedback system can alternatively include a clock and intensity sensor for recording a treatment session duration and intensity. The data received and recorded can be used by the electronic pain feedback system to evaluate the effectiveness of the pain treatment.

13 Claims, 6 Drawing Sheets

|  | DURATION OR INTENSITY | | |
|---|---|---|---|
|  | HIGH | MEDIUM | LOW |
| HIGH | BENEFIT 110 | BENEFIT 110 | BENEFIT 110 |
| MEDIUM | MARGINAL BENEFIT 112 | MARGINAL BENEFIT 112 | BENEFIT 110 |
| LOW | NO BENEFIT 114 | NO BENEFIT 114 | FURTHER TRAINING 116 |

CHANGE IN PAIN LEVEL

Fig. 6

ELECTRONIC PAIN FEEDBACK SYSTEM AND METHOD

This is a Divisional of application Ser. No. 08/527,811, filed Sept. 13, 1995 now U.S. Pat. No. 5,653,739.

BACKGROUND OF THE INVENTION

The present invention relates to a system and method for monitoring effectiveness of a pain treatment. More particularly, it relates to an electronic pain rating scale used in conjunction with a pain treatment program to provide information regarding pain treatment effectiveness based upon entry and storage of perceived levels of pain experienced by a patient.

Millions of people suffer daily from chronic pain. A variety of treatment programs have been developed to alleviate chronic pain. One such program is medicinal pain treatment. Medicinal pain treatments utilize pills or other drug-type forms.

An alternative treatment program is a transcutaneous electrical nerve stimulation (TENS). A TENS system sends carefully controlled bursts of electrical impulses into muscles and nerves at particular surface points. A mild vibrating sensation is felt by the patient using the TENS system. The pulses induce the patient's nervous system to raise its own natural substances, which prevent pain signals from reaching the brain. A TENS device can be used by a patient numerous times throughout the day whenever a patient desires pain relief.

The various pain treatments have, as a general statement, been successful in achieving both short-term and long-term pain relief. However, due to the not as of yet fully understood physiological and psychological aspects of chronic pain, validating the effectiveness of any one pain treatment has remained an elusive goal. The need for measuring the outcomes of pain treatment is becoming apparent.

A clinical outcome measurement usually takes place in a carefully controlled environment in order to reduce the number of variables to a minimum. This sort of study is very good at verifying the null hypothesis of the experiment, but the very controlled nature of the study may influence the outcome, as this "non-real world" or "lab rat" environment may introduce a hidden bias into the experiment.

Some of the clinical conditions, such as pain or psychological state of the patient cannot be measured in objective terms. Pain is the most prevalent complaint of patients and the single most frequent reason a person visits a physician, yet measurement of pain relief, and therefore quantifying treatment effectiveness, poses significant difficulties.

Presently, there are a few methods of measuring clinical pain available, such as comparison of the patient's pain with experimentally induced pain and measurement of drug dosage required to abate the pain. The most common system for measuring pain and thus for validating the effectiveness of a pain treatment program is a manually completed, pain rating scale, which appears in paper form. The manual pain rating scale is entirely separate from the particular pain treatment being used. The manual pain rating scale consists of a straight line drawn on a piece of paper, the ends of which define the extreme limits of the pain experienced. With a Verbal Descriptor Scale (VDS) a series of adjectives which describe different levels of pain are placed along the line (from "no pain" to "worst pain imaginable"). Alternatively, a Numeric Pain Scale (NPS) places a series of consecutive numbers (eg. from "1" to "10") along the line with the smallest number representing "no pain" and the largest number representing "worst pain imaginable".

There are basically two approaches for using manual pain rating scales, absolute and comparative. The absolute approach measures the severity of the pain at a particular point in time. The comparative approach provides a measurement of the change in pain over time.

When the patient periodically visits the clinician, the manual pain rating scale test is administered. The clinician provides the manual pain rating scale to the patient who then rates his or her perceived pain level on the scale provided (ie. marking the point along the continuum line, between no pain and the worst pain imaginable, where the patient's pain level falls). The clinician then collects the completed manual pain rating scale for future reference and comparison with other test results.

The manual pain rating scale is devised simply to measure the magnitude or intensity of pain at an arbitrary point in time. The manual pain rating scale may be used in conjunction with a pain treatment in an attempt to gauge the effectiveness of that treatment. However, the manual pain rating scale has a number of inadequacies.

First, the manual pain rating scale is used primarily for clinical purposes by a practiced clinician. The form is completed on the periodic occasion when a patient visits his or her clinician. Therefore, records are not kept each and every time the pain treatment is used, rendering any data taken of skewed and limited value. Second, the manual pain rating scale does not "record" the pain level before and after each pain treatment. Third, the manual pain rating scale does not take into account the level of pain treatment being administered. Fourth, the manual pain rating scale does not have the ability to store the duration of a pain treatment session.

In addition, where the manual pain rating scale is used at home by the patient, other deficiencies are encountered. These include: A) "cramming" bias, ie., do all the paperwork at once before the clinic visit; B) bias from comparison of how the pain was scored in the past; C) lost data sheets; D) lack of convenience being a demotivation; E) disincentive for a clinic to use the tool due to the huge data reduction work load of processing even a few patients; F) data errors generated in interpreting paper scales, computer entry errors, and loss of data.

The above-stated inadequacies of the manual pain rating scale greatly impede its ability to provide any meaningful feedback as to the effectiveness of the pain treatment being used. The level of pain being experienced by the patient should be measured before each and every use of the pain treatment to provide an accurate history of the patient. Similarly, the measure of change in pain level following each pain treatment session is required to accurately determine the effectiveness of the treatment. In addition, the intensity level of each pain treatment and the length of a pain treatment session are necessary to provide an adequate explanation of the overall effectiveness. Importantly, the pain and pain treatment related data should be stored to create, in effect, a diary documenting a patient's improvement and correlation of the improvement to the pain treatment employed. The manual pain rating scale simply cannot provide this data.

Therefore, a substantial need exists for a convenient system having the ability to measure and record a patient's pain level before and after each pain treatment session, along with the intensity and length of the pain treatment session.

SUMMARY OF THE INVENTION

The present invention provides an electronic pain feedback system for recording a patient's level of pain to determine overall effectiveness of a pain treatment. The system comprises an input device used in conjunction with the pain treatment. A memory device is connected to the input device to store data produced by the input device regarding the level of pain experienced by the patient. The combination of these components provide information necessary for establishing and validating the effectiveness of the pain treatment.

The input device is accessible by the patient and includes a scale having zones representing various levels of perceived pain. In response to a particular entry on the scale by the patient, the input device produces a data signal representative of the level of pain entered.

The data signal produced by the input device is received by the memory device. The memory device stores the data signal representative of the patient's perceived level of pain. In particular, the memory device will store the patient's initial level of pain prior to a pain treatment session, along with the perceived level of pain when the session is completed. In a preferred embodiment, the memory device will receive and store data signals representing duration and intensity of the pain treatment session. In the preferred embodiment, the memory device is a microcontroller which stores the pain level data for later reference. The microcontroller can also be connected to the pain treatment to facilitate its activation.

The method of using the electronic pain feedback system requires the patient to indicate on the input device the level of pain being experienced prior to beginning a pain treatment session. The level of pain data is processed by the input device, resulting in a signal which is stored in the microcontroller. Once the level of pain has been selected, the microcontroller activates the pain treatment device. Depending upon the type of pain treatment being used, the patient may at this point increase the intensity of the pain treatment to a desired level.

The pain treatment is then administered. To end the pain treatment session, the patient again enters his or her current pain level via the input device. This data point is then stored by the microcontroller. In a preferred embodiment, an intensity sensor and a clock are utilized to measure and record the intensity level of the pain treatment administered and the length of treatment time. As with the beginning and ending pain levels, these two readings are stored in the microcontroller. Over the course of several treatment sessions, enough data is accumulated to provide a correlation as to the effectiveness of the pain treatment being used.

BRIEF DESCRIPTION OF THE DRAWINGS

FIG. 6 is a chart representing a correlation of pain treatment effectiveness.

DETAILED DESCRIPTION OF THE PREFERRED EMBODIMENTS

Figure 1:
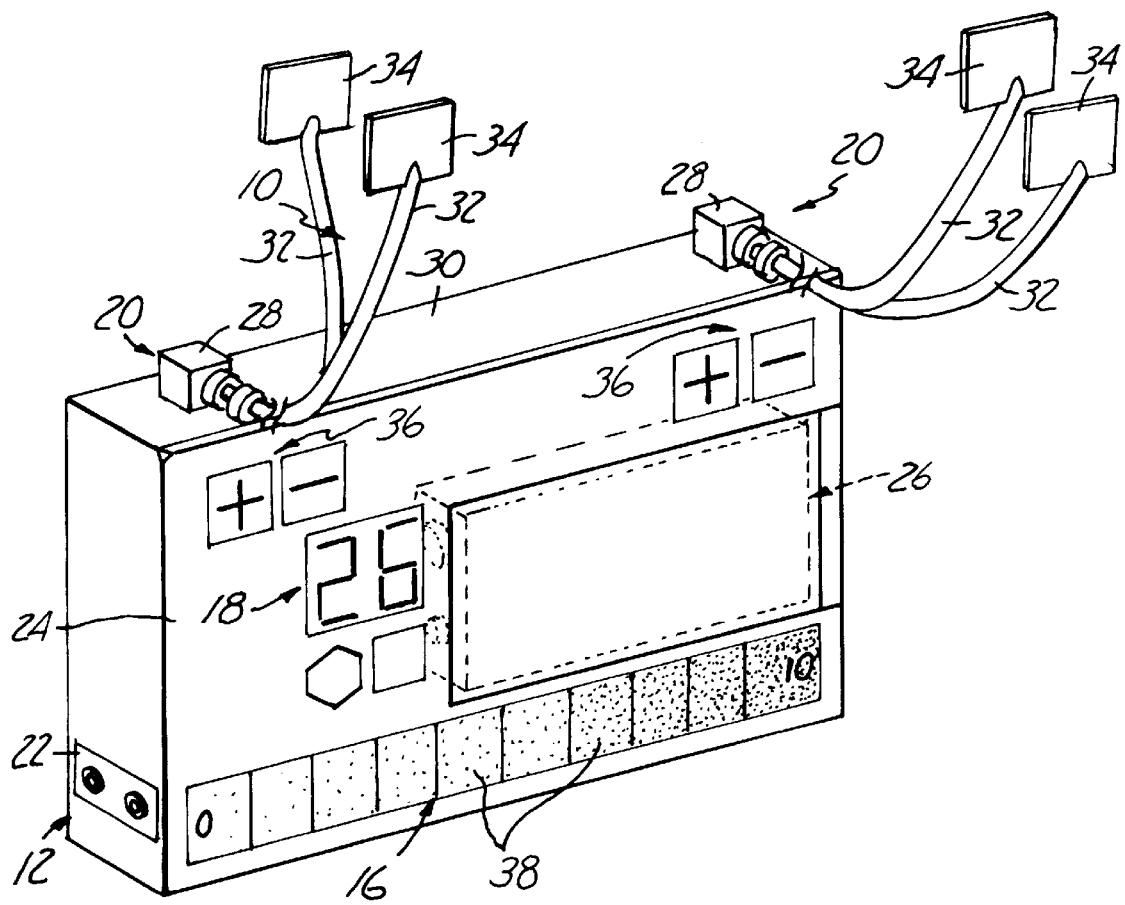
FIG. 1 is a perspective view of an electronic pain feedback system in accordance with the present invention.

A preferred embodiment of an electronic pain feedback system 10 is shown in FIG. 1. The electronic pain feedback system 10 is a modified transcutaneous electrical nerve stimulation (TENS) device and includes a case 12, a scale 16, a display 18, output channels 20 and communications port 22. The scale 16 and the display 18 are disposed on a front face 24 of the case 12.

In a preferred embodiment, the electronic pain feedback system 10 is powered by a battery 26 (shown with dashed lines) located within the case 12. As the system 10 includes a TENS device, each of the output channels 20 for the system 10 include a plug 28 inserted into a port (not shown) located on a top surface 30 of the case 12. A cable 32 extends from each plug 28 which terminates in a pair of electrodes 34. The electrodes 34 are selectively attached to a patient for administering pain treatment. Further, the output channels 20 include control buttons or keys 36 disposed on the front face 24 for controlling amplitude of stimulation. While the preferred system 10 has been shown as having two output channels 20, any other number of channels is equally acceptable.

The scale 16 is preferably a continuous membrane-type body, basically comprised of a plurality of indicating zones 38. Each of the plurality of indicating zones 38 represents a different level of perceived pain. In the preferred embodiment, the scale 16 ranges from "0" to "10", with "0" representing no pain and "10" representing the worst pain imaginable. Any other range, such as "0–100" is equally acceptable, so long as the patient is provided with a broad range in which to quantify his or her perceived level of pain. Therefore, the plurality of indicating zones 38, from left to right, represent increasing levels of perceived pain. As will later be described, depending upon which of the plurality of indicating zones 38 is selected, a representative signal is produced and stored. While the scale 16 has been shown as being a continuous membrane strip, other forms are equally acceptable. In particular, a descrete scale employing a plurality of spaced buttons could be used. Each of the buttons represents a different level of perceived pain.

The communications port 22 provides a communications link between the electronic pain feedback system 10 and any of a number of external devices (not shown). For example, the external device can include a separate computer or printer. The external device can also be a modem or other communications device such as a cellular phone which transmits data from the electronic pain feedback system 10 to another computer-based system. Thus, the communications port 22 is appropriately sized to receive a plug or similar connection means from the external device.

Figure 2:
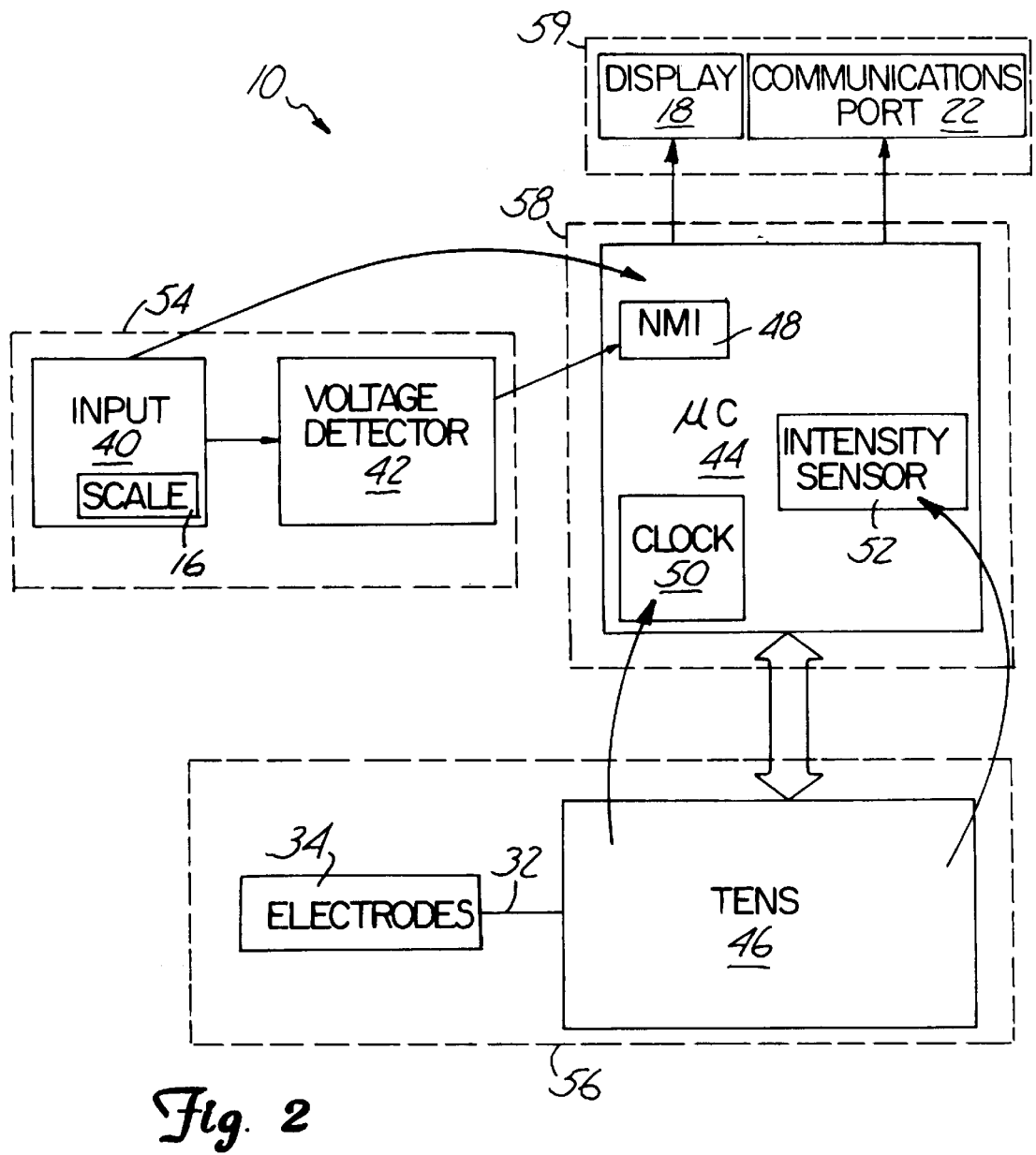
FIG. 2 is a block diagram of the electronic pain feedback system connected to a pain treatment in accordance with the present invention.

FIG. 2 is a block diagram of the electronic pain feedback system 10, providing further detail of the inner components. The electronic pain feedback system 10 includes an input device 40, a voltage detector 42, a microcontroller or memory device 44, a TENS device 46 having electrodes 34, the display 18, and the communications port 22. The input device 40 is connected to both the voltage detector 42 and the microcontroller 44. The voltage detector 42 is also connected to the microcontroller 44. The microcontroller 44 is connected to the TENS device 46, and the display 18 and the communications port 22. In the preferred embodiment, the input device 40, the voltage detector 42, the microcontroller 44, the TENS device 46, the display 18, and the communications port 22 are maintained within a single case (shown in FIG. 1 as the case 12). Furthermore, the TENS device 46 and the microcontroller 44 can be combined as a single element.

The input device 40 includes the scale 16 at which a patient's pain level is indicated. Upon entry of any information on the scale 16, the input device 40 signals the voltage detector 42 and the microcontroller 44. As will later be described in more detail, the voltage detector 42 operates to cause the microcontroller 44 to read and store the data signal from the input device 40. Finally, the TENS device 46 is connected to the microcontroller 44. Thus, the microcontroller 44 controls activation and deactivation of the TENS device 46.

The microcontroller 44 includes a non-maskable interrupt 48, a clock 50, and an intensity sensor 52. The non-maskable interrupt 48 is connected to the voltage detector 42.

The clock 50 is any known electronic real-time counting device and is connected to the TENS device 46. The clock 50 provides a time base for the microcontroller 44, which receives data regarding the time period during which the TENS device 46 is activated. This data is stored by the microcontroller 44. Although shown as part of the microcontroller 44 in FIG. 2, the clock 50 may exist separately.

Similarly, the intensity sensor 52 is connected to the TENS device 46. The intensity sensor 52 receives information from the TENS device 46 regarding the actual intensity or stimulation level of the TENS device 46. With the TENS device 46, the patient will use the control buttons 36 (shown in FIG. 1) to adjust simulation amplitude to a desired level of intensity. The intensity sensor 52 will measure the amplitude of the treatment selected. The intensity sensor 52 is connected to, or is part of, the microcontroller 44 which stores the intensity data. Although shown as part of the microcontroller 44 in FIG. 2, the intensity sensor 52 may exist separately.

As shown with broken lines in FIG. 2, the preferred electronic pain feedback system 10 is accurately described as including a patient input 54, a pain treatment 56 and a memory device 58. In the preferred embodiment, the electronic pain feedback system 10 also includes an output 59. The patient input 54 has been shown as including the input device 40 and the voltage detector 42. The pain treatment 56 is described as preferably being the TENS device 46. The microcontroller 44 and associated circuitry has been specifically alluded to as being the memory device 58. The memory device 58 is used to receive and record important information related to effectiveness of the pain treatment 56, such as beginning and ending pain levels, and can therefore take the form of a computer, microprocessor or similar device. The memory device 58 or the patient input 54 control activation and deactivation of the pain treatment 56. Finally, the output 59 can be the display 18, the communications port 22 or any other device capable of conveying a patient's pain related data to a clinician.

During use, the patient (not shown) enters his or her perceived level of pain at the input device 40 by pressing an appropriate location on the scale 16 (shown in detail in FIG. 1). The system 10 is normally powered-up, but the microcontroller 44 is maintained in a stop mode to minimize power consumption. When any position on the scale 16 is pressed, the input device 40 signals the voltage detector 42. The voltage detector 42 activates the non-maskable interrupt 48 of the microcontroller 44. When the non-maskable interrupt 48 is signalled, an interrupt service routine takes place during which pain level data from the input device 40 is read and stored in the microcontroller 44. The microcontroller 44 then activates the TENS device 46 and the clock 50.

Once the TENS device 46 is initiated, the patient (not shown) sets the desired level of pain treatment stimulation by manipulating the control buttons 36 (shown in FIG. 1). The intensity sensor 52 senses the intensity or amplitude of the stimulation produced by the TENS device 46, and records the final stimulation level. The intensity sensor 52 transfers this intensity data to the microcontroller 44 where it is stored.

To terminate the treatment session, the patient indicates on the scale 16 his or her perceived pain level. The input device 40 then signals the voltage detector 42 and in turn the non-maskable interrupt 48. The microcontroller 44 stops the clock 50 which has been maintaining real-time running count (or duration) data for the treatment session. The treatment session duration data is signalled by the clock 50 to the microcontroller 44 where it is stored. Similarly, the intensity level of the treatment session data is signalled from the intensity sensor 52 to the microcontroller 44, as is the ending pain level.

The various data stored by the microcontroller 44 (such as beginning pain level, ending pain level, duration and intensity) is available for review by a clinician (not shown) via the display 18 or the communications port 22. This data can be in raw form, or the microcontroller 44 will include analysis software to correlate the data. In whatever form desired, the clinician can review the data at a location remote from the patient by attaching a communications line or other electronic information exchange means to the communications port 22 to transmit the data.

The microcontroller 44 is typically a microprocessor with associated memory and interface circuitry, and can be any of a multitude of controllers available to one skilled in the art, so long as it is able to receive and store information In practice, as shown in FIG. 1, the microcontroller 44 is built into a standard TENS device as is the input device 40 (including the scale 16).

The electronic pain feedback system 10 of FIG. 2 has been described as preferably including the voltage detector 42. This is used to minimize power consumption. However, it should be readily understood that the voltage detector 42 need not be employed. The input device 40 can deliver pain level data directly to the microcontroller 44, which could be powered up at all times and ready to receive and store the signalled data. The microcontroller 44 would not require the non-maskable interrupt 48 in such a system configuration.

Figure 3:
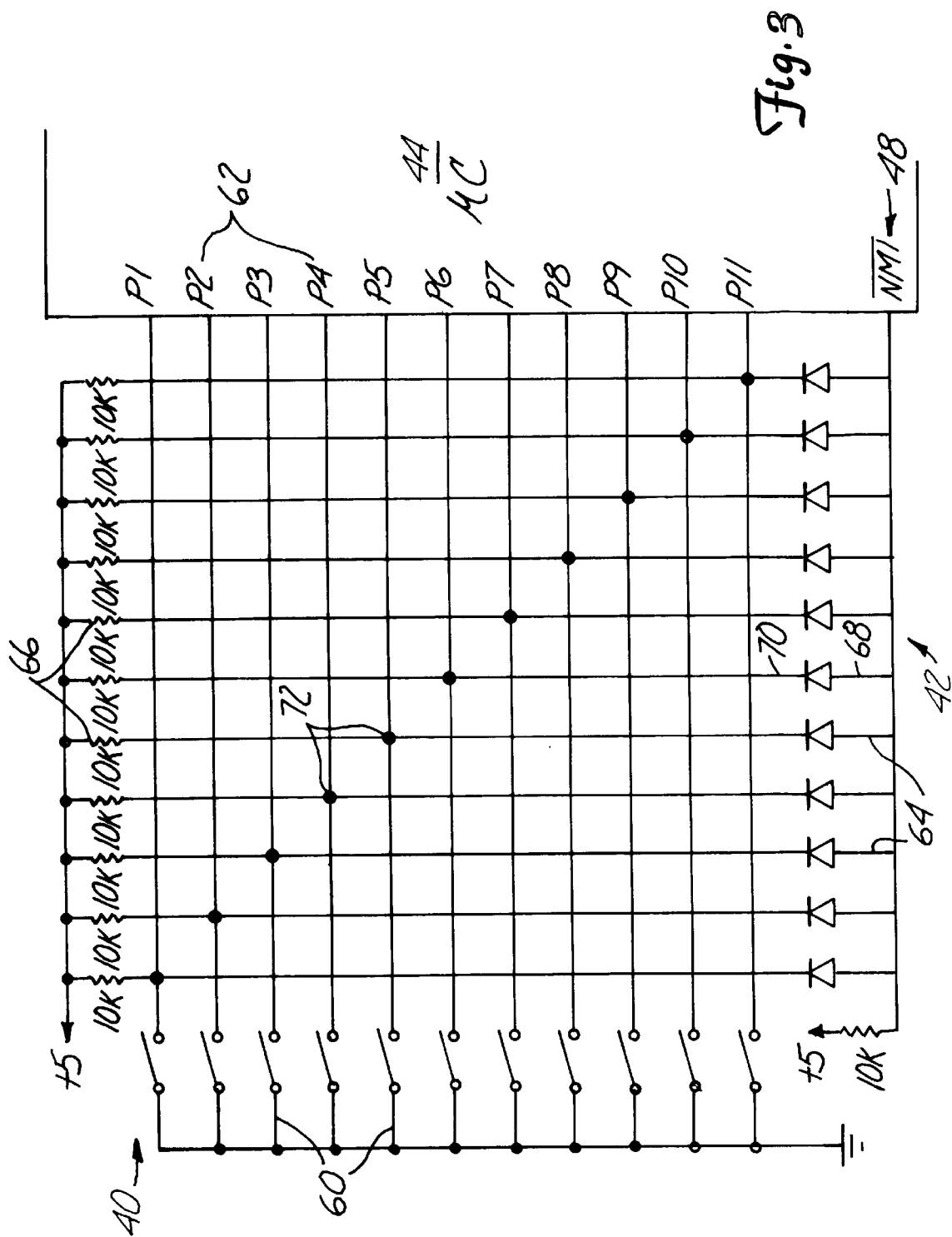
FIG. 3 is a schematic of an electronic pain feedback system.
Figure 4:
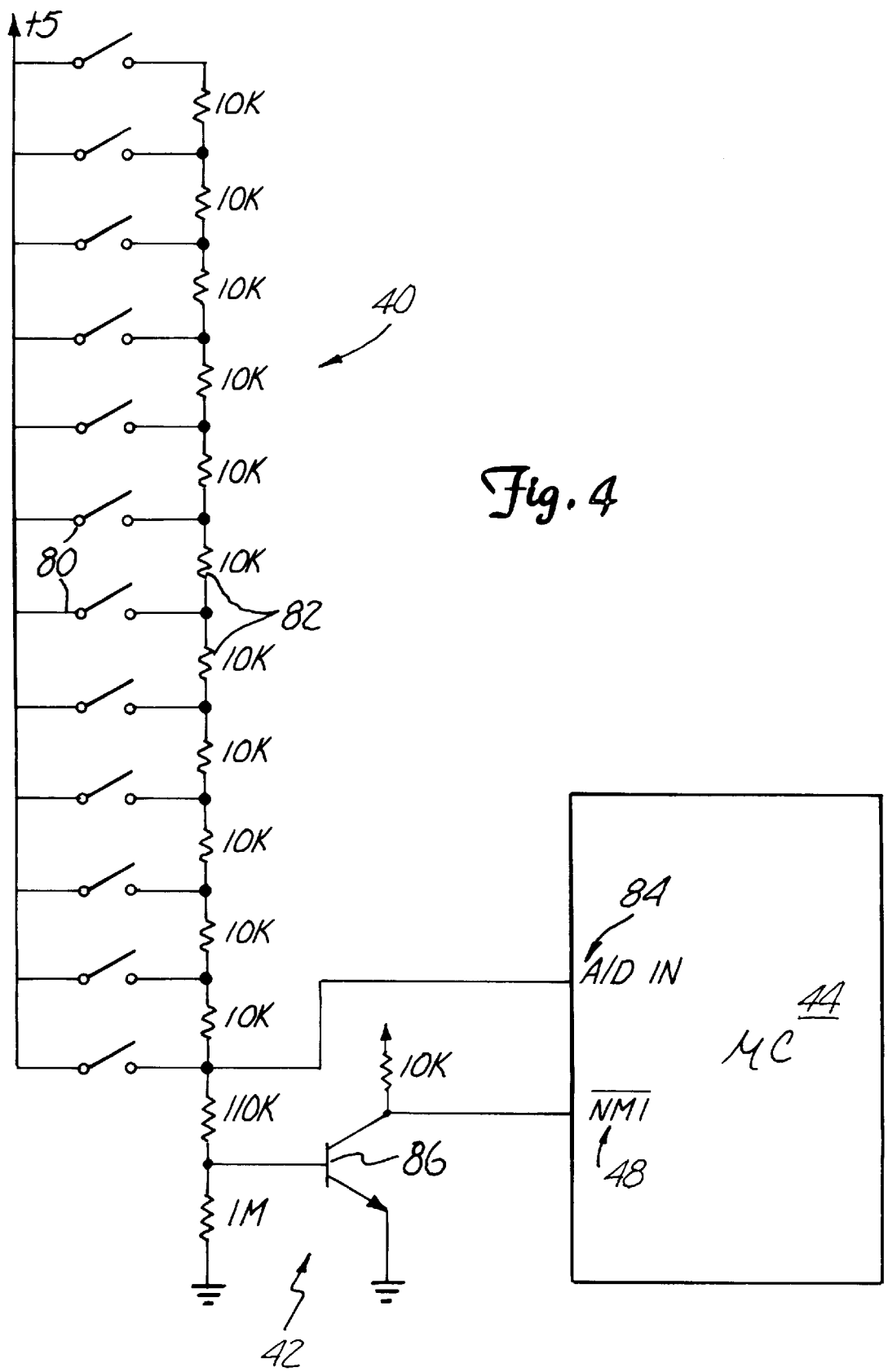
FIG. 4 is an alternative schematic of an electronic pain feedback system.
Figure 5:
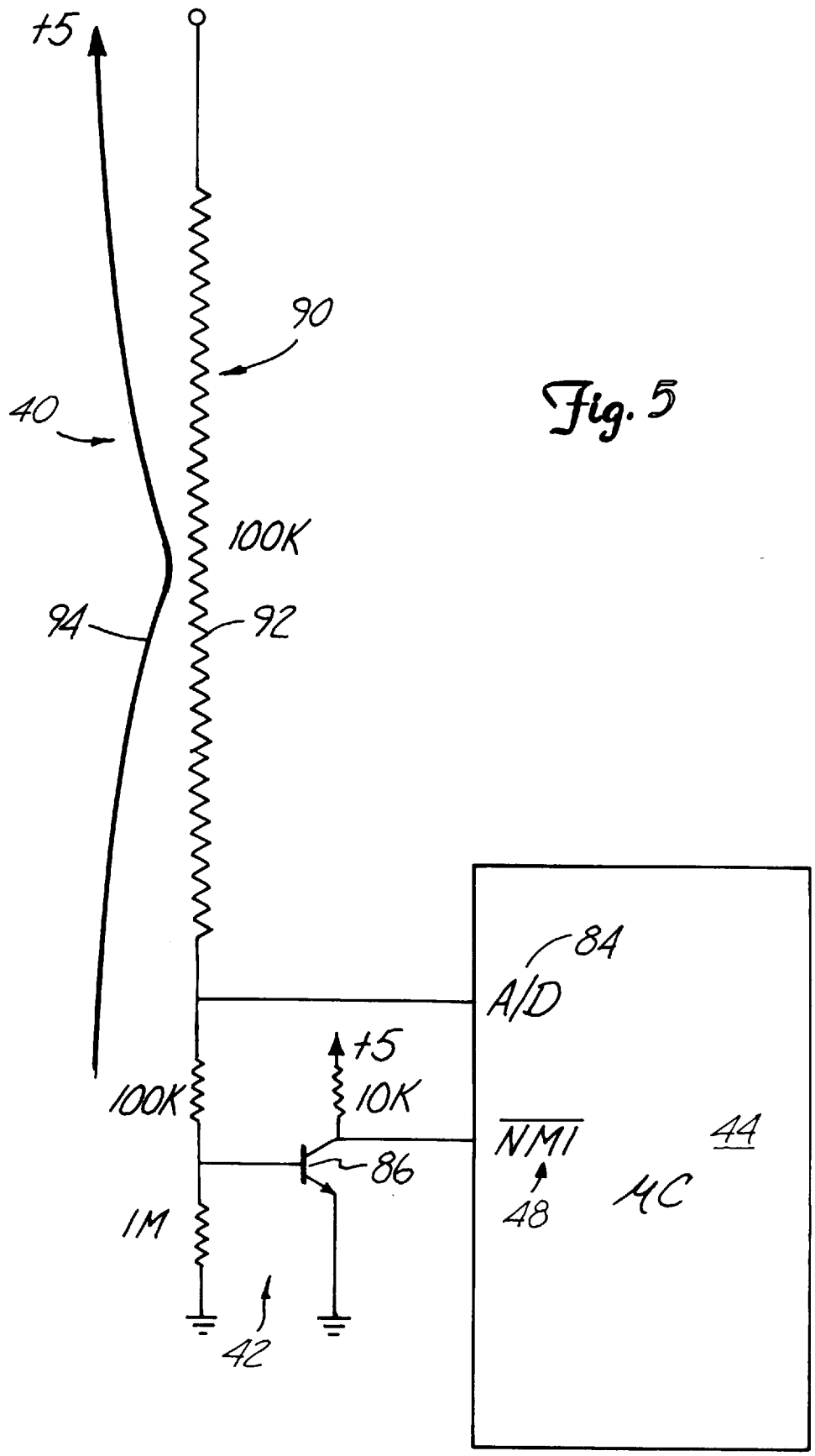
FIG. 5 is a alternative schematic of an electronic pain feedback system.

FIGS. 3–5 are schematic diagrams of the input device 40 and the voltage detector 42 using various circuitry configurations. FIG. 3 shows a digital version of the electronic pain feedback system 10. The input device 40 is comprised of a plurality of switches 60 and a plurality of digital input ports 62 on the microcontroller 44. When closed, each of the plurality of switches 60 is connected to one of the plurality of digital input ports 62 on the microcontroller 44. The plurality of switches 60 corresponds with the scale 16 (shown in FIG. 1).

The voltage detector 42 is comprised of a plurality of diodes 64 and a plurality of resistors 66. Each of the plurality of diodes 64 has an anode 68 and a cathode 70, the cathode 70 being connected to one of the plurality of resistors 66. The anode 68 of each of the plurality of diodes 64 is connected to the non-maskable interrupt 48 of the microcontroller 44. As depicted in FIG. 3, there are the same number of the switches 60, the digital input ports 62, the diodes 64 and the resistors 66. Further, a plurality of connection points 72 are created by the contact between an individual switch 60/individual input port 62 connection and an individual diode 64/individual resistor 66 connection.

In practice, a patient (not shown) will depress or close one of the plurality of switches 60 representing his or her perceived level of pain. When one of the plurality of switches 60 is depressed, the respective connection point 72 energizes a diode 64/resistor 66 connection, pulling the non-maskable interrupt 48 of the microcontroller 44 low. During the interrupt service routine, the microcontroller 44 reads the state of the digital inputs ports 62 to determine which of the plurality of switches 60 was depressed. The pain level data associated with that particular switch 60 is stored by the microcontroller 44 as initial pain level data.

Following entry and storage of the initial pain level data by the microcontroller 44, the TENS device 46 (shown in FIG. 2) administers treatment to the patient (not shown). To end the treatment, the patient must depress or close one of the plurality of switches 60 representing his or her perceived level of pain. The microcontroller 44 reads the state of the digital input ports 62 to determine which of the plurality of switches 60 was depressed. The pain level associated with that particular switch 60 is stored by the microcontroller 44 as ending pain level data. The microcontroller 44 then deactivates the TENS device 46 (shown in FIG. 2). In addition, as previously discussed, the duration and intensity of the treatment can be stored by the microcontroller 44.

An alternative embodiment of the input device 40 and the voltage detector 42 is shown in FIG. 4. The system shown in FIG. 4 employs an analog version using a keyboard for the scale 16 (shown in FIG. 1). The input device 40 is comprised of a plurality of switches 80, connected in parallel, and a plurality of resistors 82 separating the switches 80. The circuitry is connected to an analog/digital converter input 84 of the microcontroller 44. Further, the input device 40 is connected to the voltage detector 42, which consists of a transistor 86. The transistor 86 is connected at its collector to the non-maskable interrupt 48 of the microcontroller 44.

Much like the digital version presented in FIG. 3, the circuit depicted in FIG. 4 is normally powered-up, but the microcontroller 44 is stopped so that power consumption is minimal. When any of the plurality of switches 80 is depressed, the transistor 86 activates the non-maskable interrupt 48. During the interrupt service routine, the microcontroller 44 reads the voltage level at the analog/digital converter input 84 to determine which of the plurality of switches 80 was depressed. The pain level associated with the switch 80 is then stored by the microcontroller 44 as initial pain level data for future reference.

Following entry and storage of the initial pain level data by the microcontroller 44, the TENS device 46 (shown in FIG. 2) administers treatment to the patient (not shown). To end the treatment, the patient must depress one of the plurality of switches 80 representing his or her perceived level of pain. The microcontroller 44 reads the voltage level at the analog/digital converter input 84 to determine which of the plurality of switches 80 was depressed. The pain level associated with that particular switch 80 is stored by the microcontroller 44 as ending pain level data. The microcontroller 44 then deactivates the TENS device 46 (shown in FIG. 2).

FIG. 5 presents an alternative analog version of the input device 40. The input device 40 is comprised of a continuous analog control 90 which is shown as a resistor 92 and a powered membrane 94. The resistor 92 is connected to the analog/digital converter input 84 of the microcontroller 44. Further, the resistor 92 is connected to the voltage detector 42 which consists of the transistor 86 connected to the non-maskable interrupt 48 of the microcontroller 44.

The device shown in FIG. 5 is equivalent electrically to that shown in FIG. 4, except that the continuous analog control 90 is used instead of the discrete switches 80 (of FIG. 4). When the patient (not shown) presses the powered membrane 94, thus contacting the resistor 92, the voltage detector 42 activates the non-maskable interrupt 48, causing a non-maskable interrupt to occur. During the interrupt service routine, the microcontroller 44 reads the voltage level of the input device 40 at the analog/digital converter input 84 to determine the location of the point where the continuous analog control 90 was pressed. This data, representative of pain level, is then stored in the microcontroller 44 as initial pain level data.

Following entry and storage of the initial pain level data by the microcontroller 44, the TENS device 46 (shown in FIG. 2) administers treatment to the patient (not shown). To end the treatment session, the patient must depress a point along the continuous analog control 90 representing his or her perceived level of pain. The microcontroller 44 reads the voltage level at the analog/digit converter input 84 to determine the location of the point where the continuous analog control 90 was pressed. The pain level associated with that particular position is stored by the microcontroller 44 as ending pain level data. The microcontroller 44 then deactivates the TENS device 46 (shown in FIG. 2).

The stored data (e.g. initial pain level, ending pain level, duration and intensity of the treatment session) can be reported to a clinician at the end of a single treatment session or series of treatment sessions. In one embodiment, the microcontroller 44 will analyze the information, calculate an evaluation of pain treatment effectiveness. For example, where only the initial pain level and ending pain level are recorded, the microcontroller 44 will calculate change in pain level for each session. Depending on the amount of change, an index number will be assigned to that particular session. A larger index number would represent a significant reduction in the perceived pain level, whereas a smaller number would be assigned to an unchanged or increased pain level. With this approach, a series of large index numbers will indicate that the pain treatment was effective. Alternately, instead of index numbers, ordinal signs (eg. "−" for decrease in pain, regardless of magnitude; "+" for increase in pain, regardless of magnitude; and "0" for no change in pain level) will be used. By analyzing a series of the ordinal signs over time, the microcontroller is able to calculate the effectiveness of the pain treatment.

In a second embodiment, where duration of the treatment session and/or intensity are also recorded, the microcontroller 44 will perform further correlations to better evaluate effectiveness of the pain treatment. For example, the change in pain level during a treatment session will be calculated. Depending upon the degree of change, a classification of "High," "Medium," or "Low" is assigned, with "High" representing a large decrease in perceived pain, "Medium" representing a lesser decrease in perceived pain, and "Low" representing no change or an increase in perceived pain. This change in pain level classification is then used as one dimension in a two dimensional matrix, with the other dimension being the duration of the treatment session or the intensity of the treatment session.

As shown by the chart in FIG. 6, the duration or intensity is assigned a "High," "Medium," or "Low" classification. Depending upon the results, a clinician learns whether the pain treatment was effective (area 110), marginal (area 112), not effective (area 114), or that the patient needs further training on the pain treatment's use (area 116). Further, an index number will be assigned to each matrix point, so that a series of results is received and outputted. From this information, a statistical trend is created and a P valve is calculated. Numerous other ways of correlating/evaluating the data are equally available, such as algorithms or other matrices.

For example, in a third embodiment, a slope value (S) is calculated which is equal to the change in a patient's pain level (▲P) during a particular session over the intensity (I) or duration (T) reading from the session, multiplied by a constant (K) (ie. S=(▲P/I or T)*K). If the slope value S is greater than a predetermined value, then the pain treatment used is highly effective. If the slope value S falls between two intermediate values, the pain treatment used is of average effectiveness. Finally, if the slope value S is less than a predetermined number, the pain treatment is only marginally effective.

The electronic pain feedback system 10 is a simple, low cost device which allows real-time measurement of subjective perceptions or sensations and provides invaluable data for determining the effectiveness of a pain treatment. The system is easy to use and allows measurements to be made in the "real world" of the patient, ie. in the home or at work. Further, the system forces the patient to consistently enter pain level data, as the TENS device is only activated and deactivated upon entry of information on the scale. The output from the system can be used in a wide variety of applications and can provide a statistical correlation for evaluating a pain treatment and/or the consistency of the patient's response. The instrument will automatically calculate statistical parameters, such as a trend of the patient's pain and a histogram of the patient's pain levels grouped daily, weekly or monthly.

Although the present invention has been described with reference to preferred embodiments, workers skilled in the art will recognize that changes may be made in form and detail without departing from the spirit and scope of the invention. As previously described, the present invention involves the use of an input device and memory device in conjunction with a pain treatment to create an electronic diary of a patient's responsiveness to and evaluate the effectiveness of a particular pain treatment. Thus, a pain treatment or therapeutic method can be used in place of the preferred TENS device. A medicinal treatment can be employed whereby the patient enters a beginning pain level on the electronic pain rating scale prior to taking the medicine. An ending pain level is similarly entered by the patient after a predetermined length of time. This data is then used to ascertain the effectiveness of the pain treatment.

Finally, while three examples of possible circuitry for the input device and the voltage detector have been provided, any other configuration is acceptable. The input device and the voltage detector are simply used to provide the patient with a convenient means for entering perceived pain level data.

What is claimed is:

1. A method of evaluating effectiveness of a pain treatment for a patient, the method comprising:
   entering a beginning level of pain experienced by the patient on an electronic pain rating device;
   administering the pain treatment to the patient;
   entering an ending level of pain on the electronic pain rating device;
   receiving pain related data from the electronic pain rating device representing the levels of pain experienced by the patient;
   correlating the pain related data according to change in the level of pain experienced by the patient; and
   providing an output wherein the output evaluates effectiveness of the pain treatment.

2. The method of evaluating effectiveness of a pain treatment of claim 1, wherein correlating the pain related data includes:
   measuring duration of a pain treatment session;
   comparing first data representing a first level of pain experienced by the patient with second data representing a second level of pain experienced by the patient to determine the change in the level of pain experienced by the patient; and
   comparing the change in the level of pain experienced by the patient with the duration of the pain treatment session.

3. The method of evaluating effectiveness of a pain treatment of claim 1, wherein correlating the pain related data includes:
   measuring intensity of a pain treatment session;
   comparing first data representing a first level of pain experienced by the patient with second data representing a second level of pain experienced by the patient to determine the change in the level of pain experienced by the patient; and
   comparing the change in the level of pain experienced by the patient with the intensity of the pain treatment session.

4. A method of evaluating effectiveness of a pain treatment for a patient, the method comprising:
   entering a first level of pain, experienced by the patient at a first time relative to the pain treatment, on an electronic pain rating device;
   administering a pain treatment entering a second level of pain, experienced by the patient at a second time relative the pain treatment, on the electronic pain rating device;
   receiving pain related data from the electronic pain rating device representing the first level of pain experienced by the patient at a first time relative to the pain treatment and a second level of pain experienced by the patient at a second time relative to the pain treatment;
   comparing data representing the first level of pain experienced by the patient at the first time relative to the pain treatment with data representing the second level of pain experienced by the patient at the second time relative to the pain treatment to determine a change in the level of pain experienced by the patient; and
   providing an output which is a function of the change in the level of pain.

5. The method of evaluating effectiveness of a pain treatment of claim 4, and further comprising:
   measuring duration of a pain treatment session.

6. The method of claim 4, and further comprising:
   measuring intensity of a pain treatment during a pain treatment session.

7. A method of evaluating effectiveness of a pain treatment for a patient, the method comprising:
   entering a plurality of pain levels, experienced by the patient at different times during each of a plurality of pain treatment, on an electronic pain rating device;
   receiving pain related data from the electronic pain rating device representing a level of pain experienced by a patient at different times during each of a plurality of pain treatment sessions;
   determining a change in the level of pain experienced by the patient during each of the pain treatment sessions based upon pain related data received at different times during that pain treatment sessions; and
   providing an output based upon the changes in the level of pain.

8. The method of evaluating effectiveness of a pain treatment of claim 7, and further comprising:

measuring duration of each pain treatment session; and providing an output based upon the measured durations.

9. The method of evaluating effectiveness of a pain treatment of claim 8, and further comprising:

measuring intensity of pain treatment during each pain treatment session;

providing an output based upon the measured intensities.

10. A method of evaluating effectiveness of a pain treatment for a patient, the method comprising:

entering a level of pain, experienced by the patient at the beginning of a pain treatment session, on an electronic pain rating device;

administering the pain treatment session;

entering a level of pain experienced by the patient at the end of the pain treatment session, on the electronic pain rating device;

receiving pain related data from the electronic pain rating device representing a level of pain experienced by a patient at the beginning and at the end of the pain treatment session;

determining a change in the level of pain experienced by the patient during the pain treatment based upon the pain related data; and providing an output based upon the change in the level of pain.

11. The method of claim 10, and further comprising:

measuring duration of the pain treatment session.

12. The method of claim 10, and further comprising:

measuring intensity of a pain treatment during the pain treatment session.

13. The method of claim 10, wherein providing the output is based upon the change in level of pain, the duration of the pain treatment session and the intensity of the pain treatment.

* * * * *